(12) United States Patent
Seong et al.

(10) Patent No.: US 8,084,502 B2
(45) Date of Patent: Dec. 27, 2011

(54) USE OF AGMATINE FOR PROTECTION OF RETINAL GANGLION CELLS

(76) Inventors: Gong Je Seong, Seoul (KR); Chan Yun Kim, Seoul (KR); Jong Eun Lee, Seoul (KR); Samin Hong, Seoul (KR)

( * ) Notice: Subject to any disclaimer, the term of this patent is extended or adjusted under 35 U.S.C. 154(b) by 0 days.

(21) Appl. No.: 12/594,812

(22) PCT Filed: Apr. 3, 2008

(86) PCT No.: PCT/KR2008/001879
§ 371 (c)(1),
(2), (4) Date: Jan. 14, 2010

(87) PCT Pub. No.: WO2008/123684
PCT Pub. Date: Oct. 16, 2008

(65) Prior Publication Data
US 2010/0130783 A1    May 27, 2010

(30) Foreign Application Priority Data

Apr. 4, 2007   (KR) .................... 10-2007-0033367

(51) Int. Cl.
*A61K 31/155* (2006.01)
*C07C 279/12* (2006.01)
(52) U.S. Cl. ........................................ 514/634; 564/240
(58) Field of Classification Search .................. None
See application file for complete search history.

(56) References Cited

U.S. PATENT DOCUMENTS

| 5,574,059 | A | * | 11/1996 | Regunathan et al. | ......... 514/397 |
| 6,066,675 | A |   | 5/2000  | Wen et al.        |                   |
| 6,114,392 | A | * | 9/2000  | Gilad et al.      | .................. 514/634 |

FOREIGN PATENT DOCUMENTS

WO    WO 99/08669    2/1999

OTHER PUBLICATIONS

The Merck Index 14th ed. version 14.6, O'Neil, Maryadele J. et al editors, 2006, 2010 Merck Sharp & Dohme Corp., a subsidiary of Merck & Co., Inc., Whitehouse Station, NJ, entry No. 00188 Agmatine.*
Hong, Samin et al. "Agmatin protects retinal ganglion cells from hypoxia-induced apoptosis in transformed rat retinal ganglion cell line." BMC Neuroscience. Oct. 2, 2007, Vol.8, No. 81, pp. 1-11.

* cited by examiner

*Primary Examiner* — Brian J Davis
(74) *Attorney, Agent, or Firm* — Mannava & Kang, PC; Hyunho Park

(57) ABSTRACT

A use method of agmatine or a pharmaceutically allowable salt thereof, and a pharmaceutical composition comprising the same are disclosed. The method and pharmaceutical composition of the present invention can effectively cure or prevent eye diseases preferably including glaucoma, retinopathy, and optic neuropathy associated with apoptosis in retinal ganglion cells (RGCs), particularly hypoxia-induced or tumor necrosis factor-$\alpha$ (TNF-$\alpha$)-induced apoptosis.

10 Claims, 11 Drawing Sheets

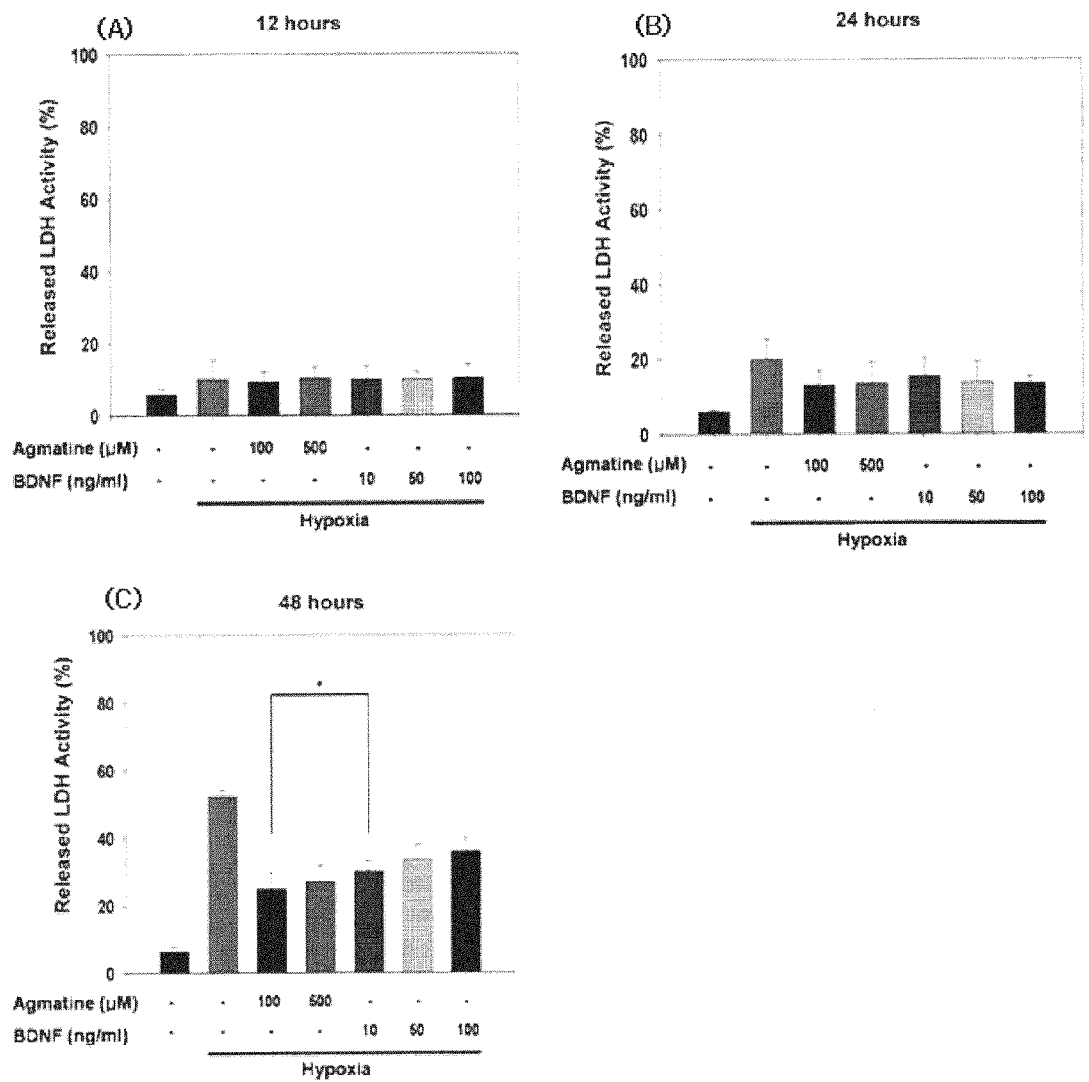
[Fig. 1]

[Fig. 2]
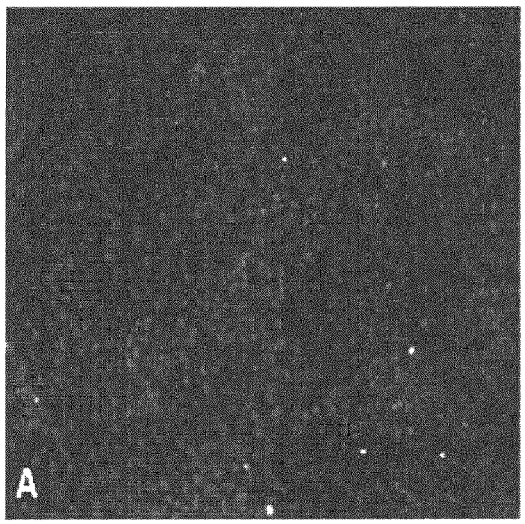
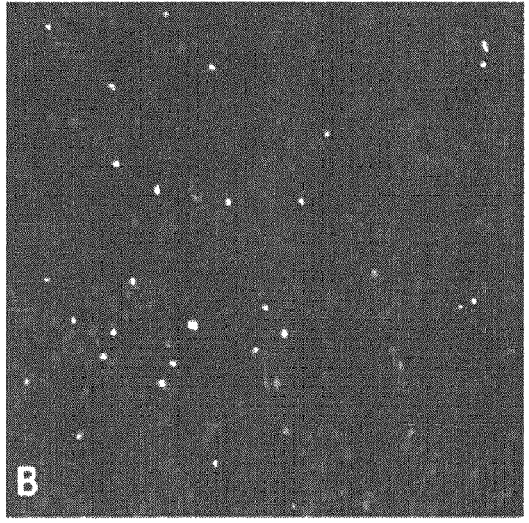
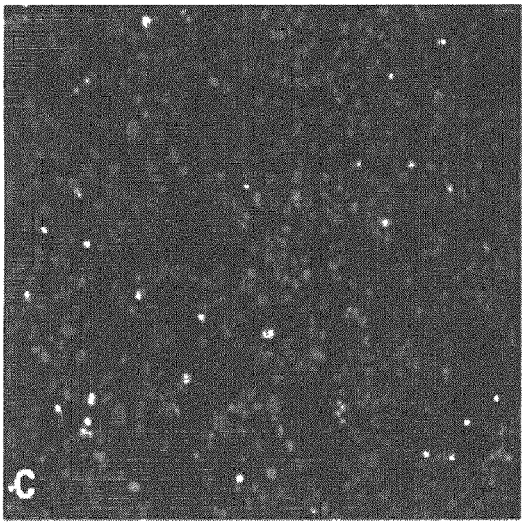
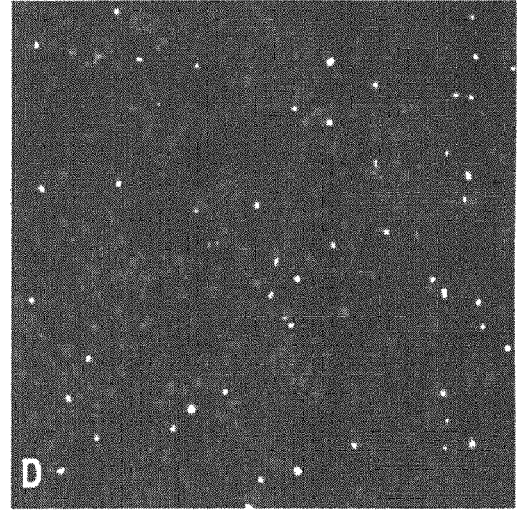

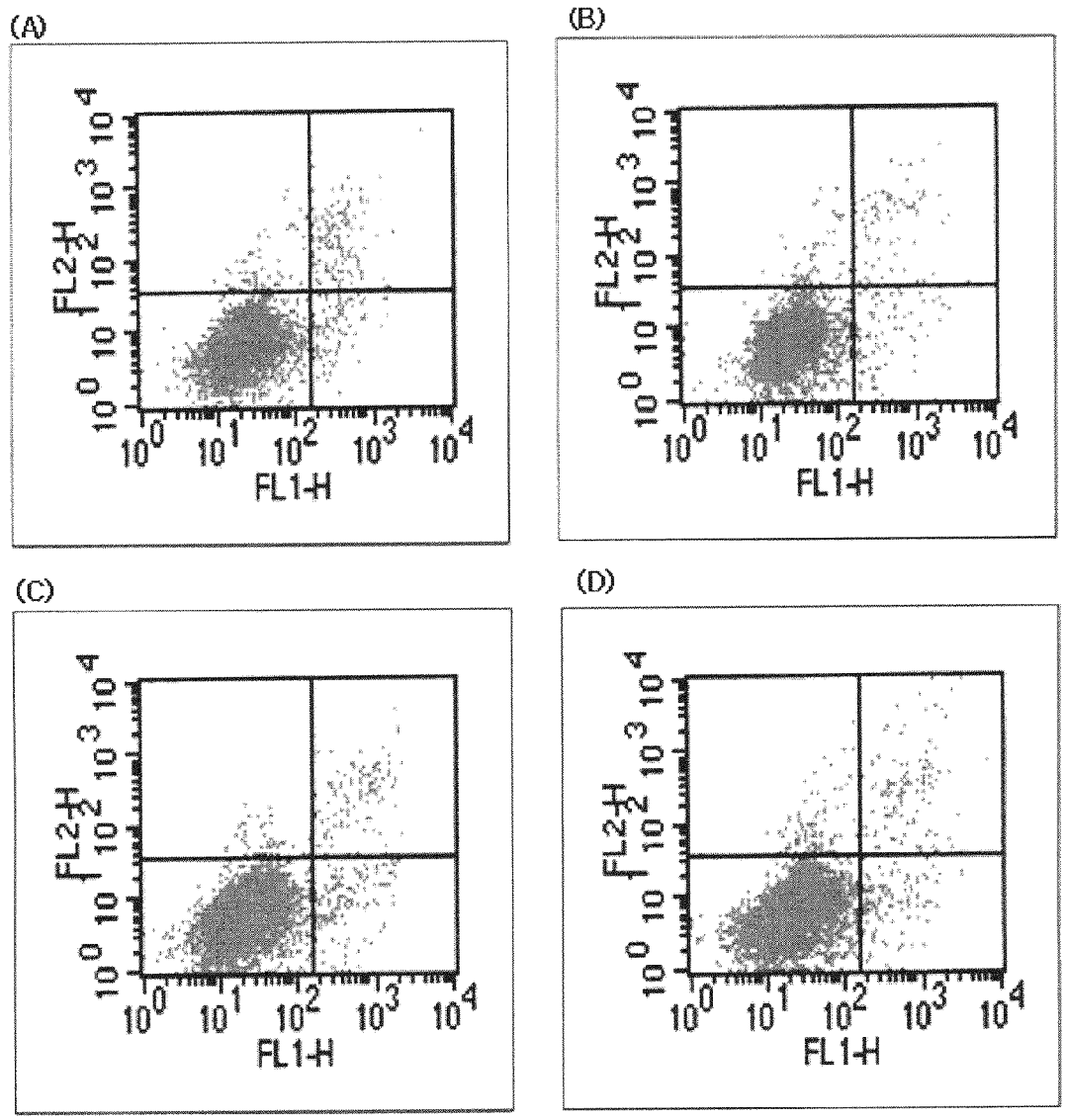

[Fig. 4]
(A) 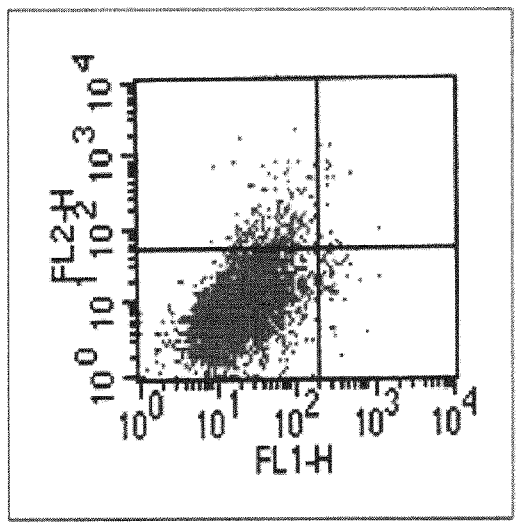
(B) 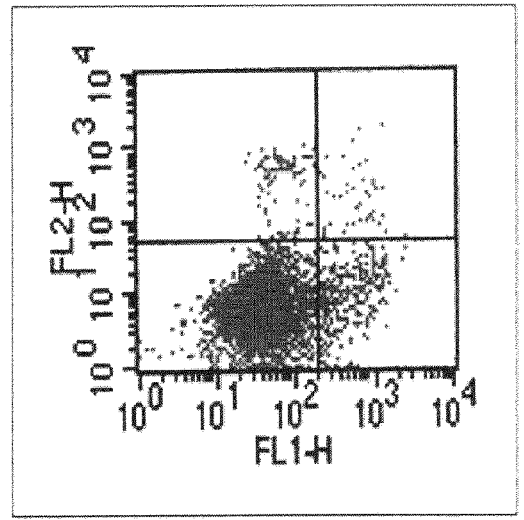
(C) 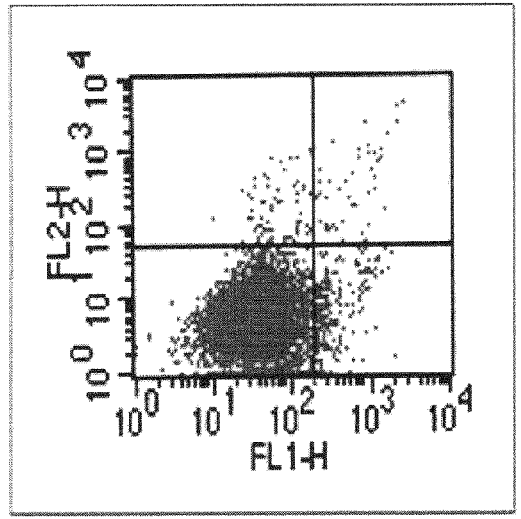
(D) 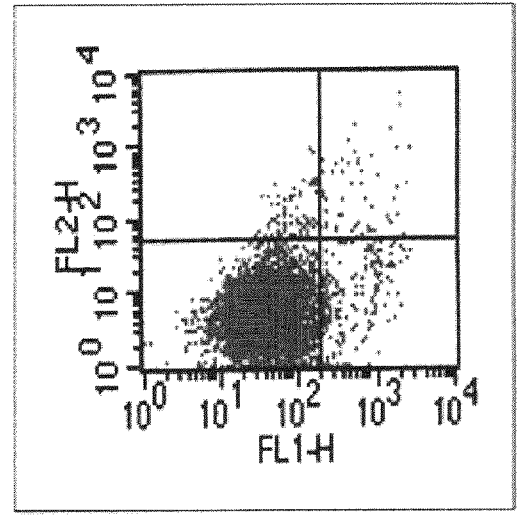

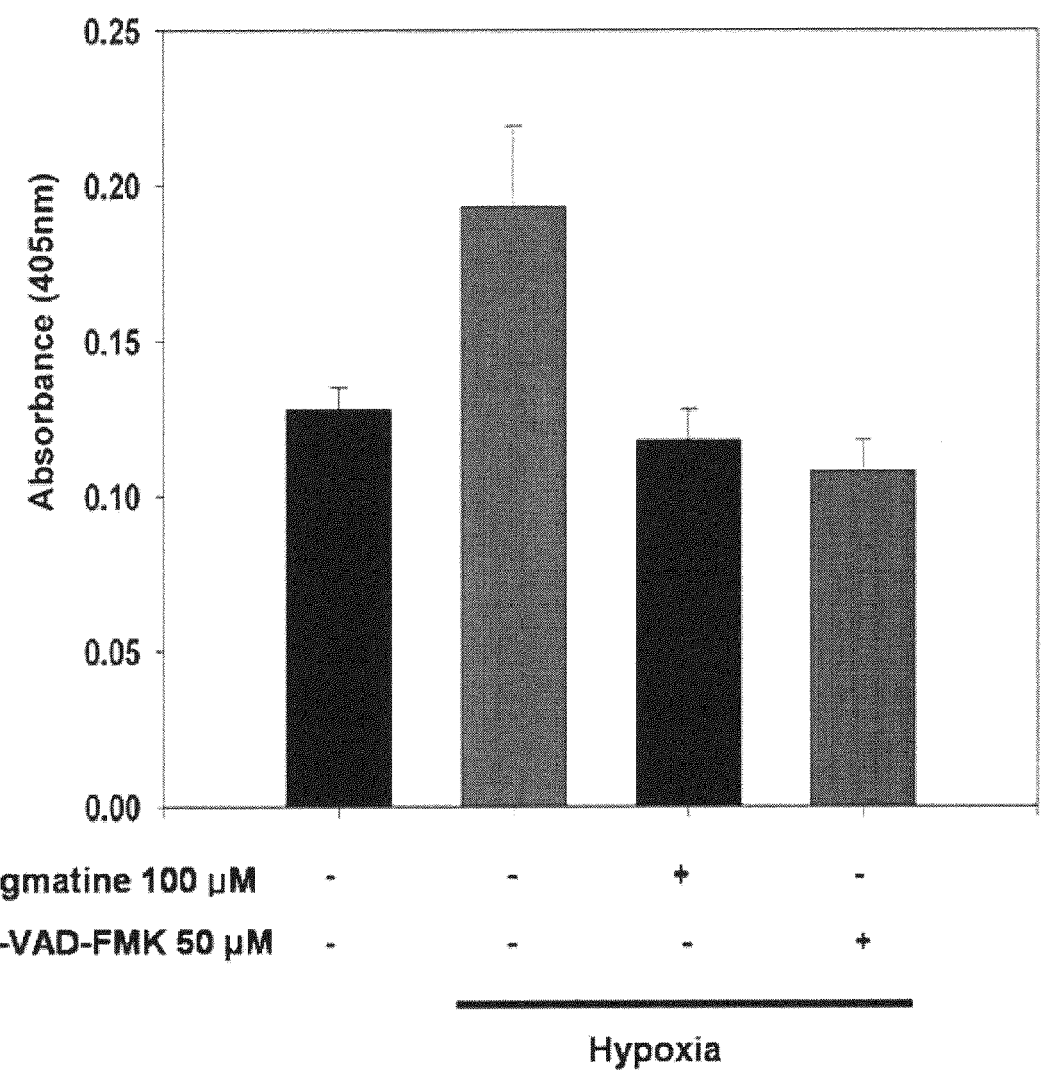
[Fig. 5]

[Fig. 6]
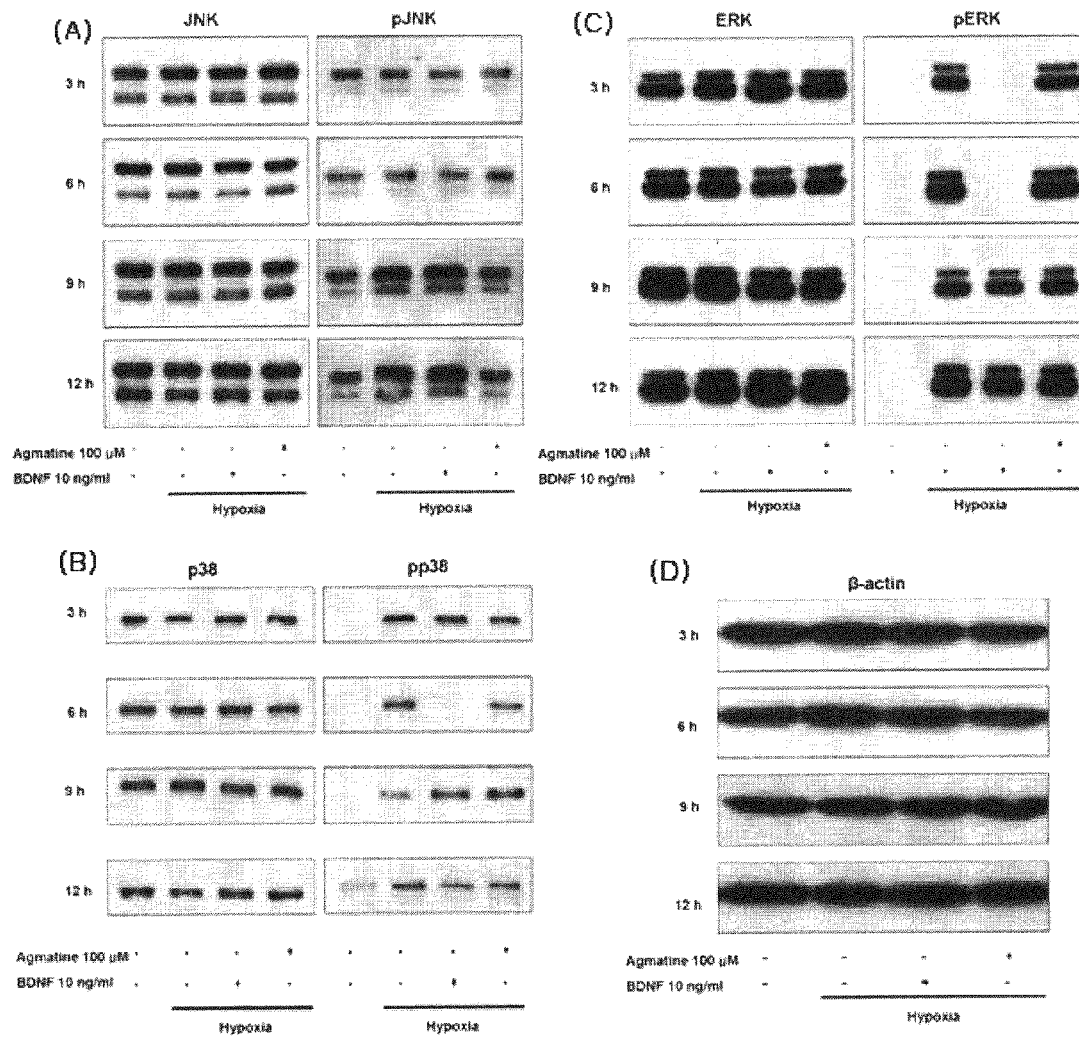

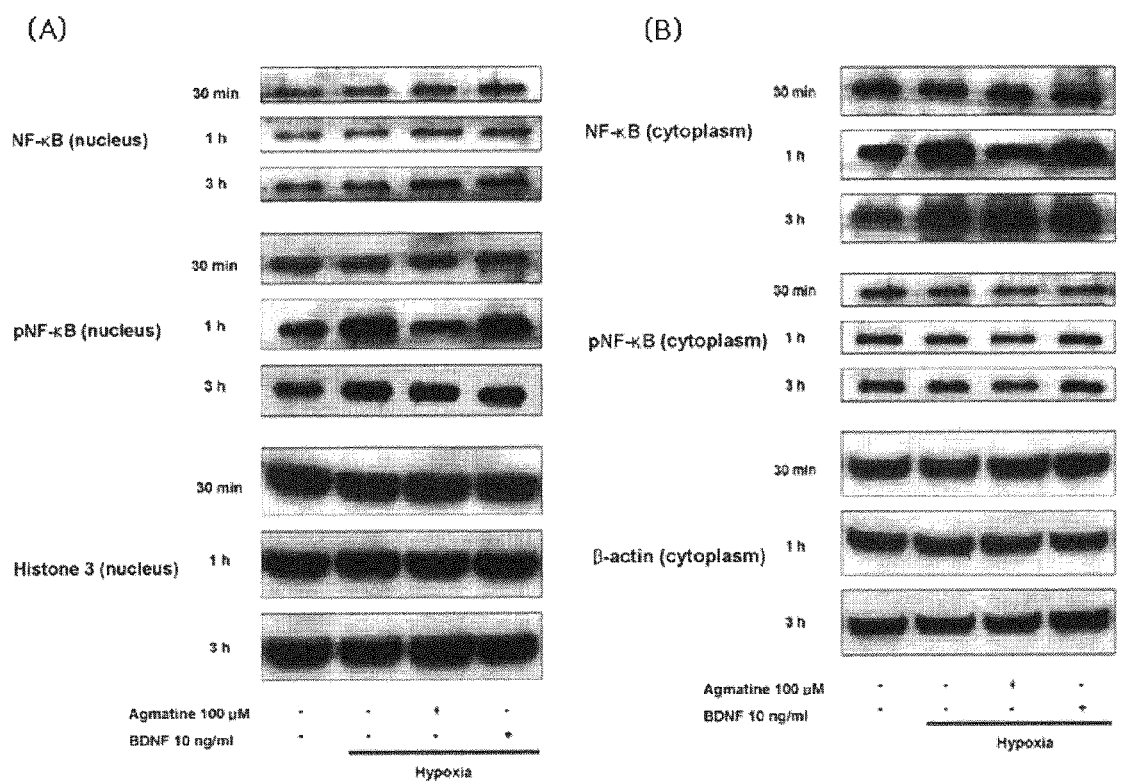
[Fig. 7]

[Fig. 8]
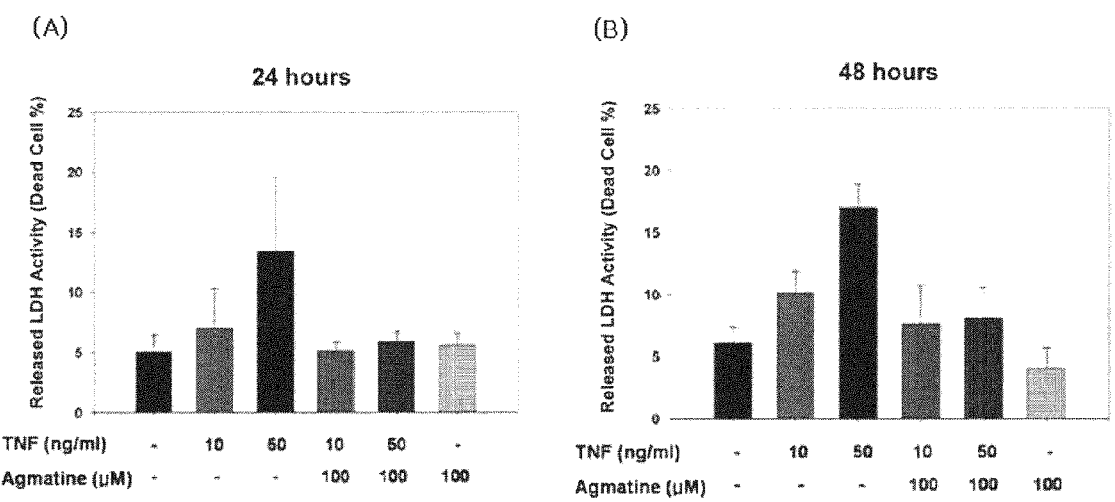

[Fig. 9]
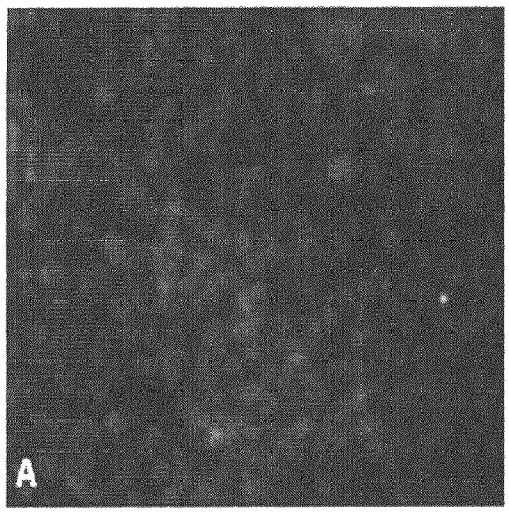
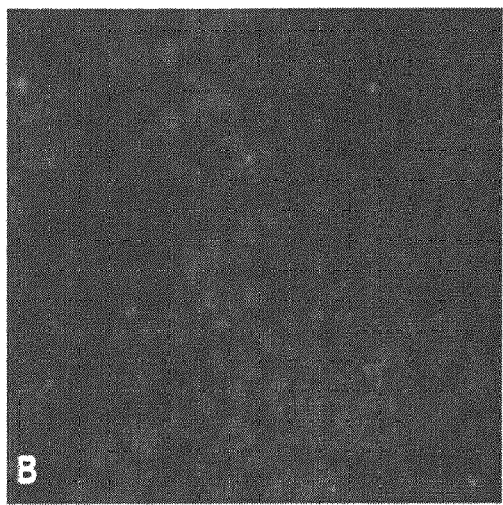
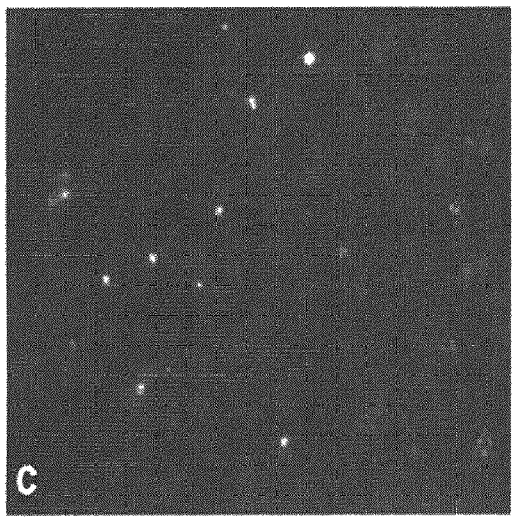
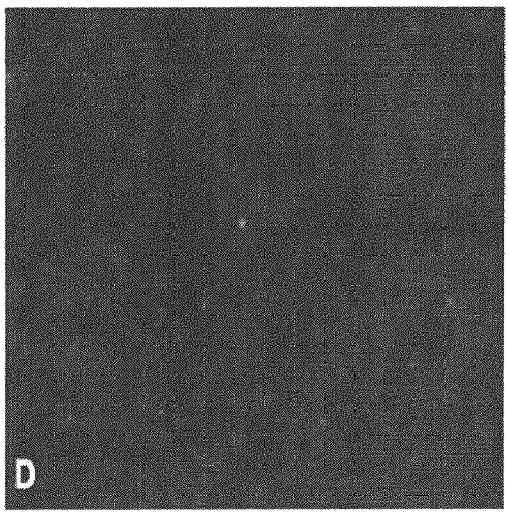

[Fig. 10]
(A)
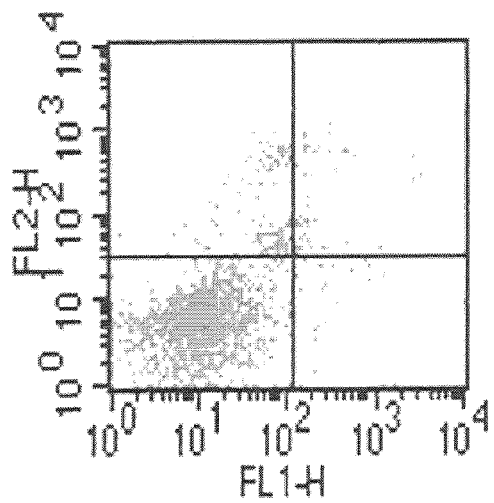
(B)
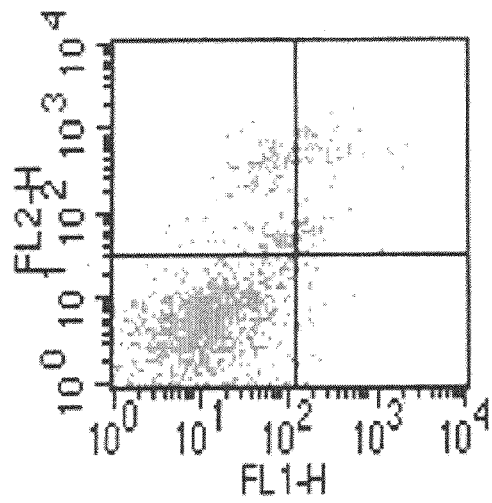
(C)
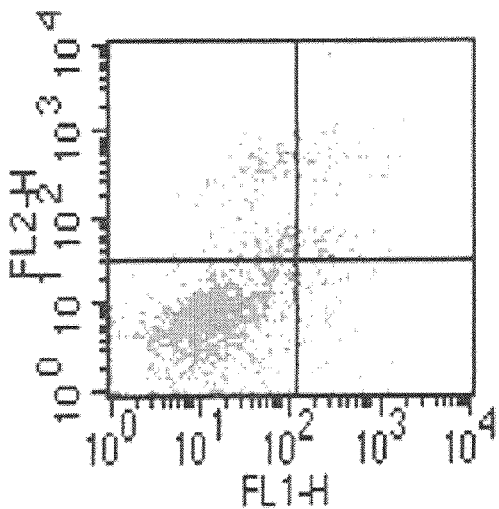
(D)
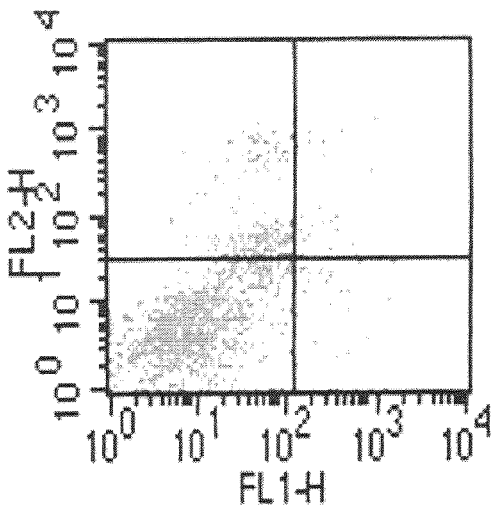

[Fig. 11]
(A)
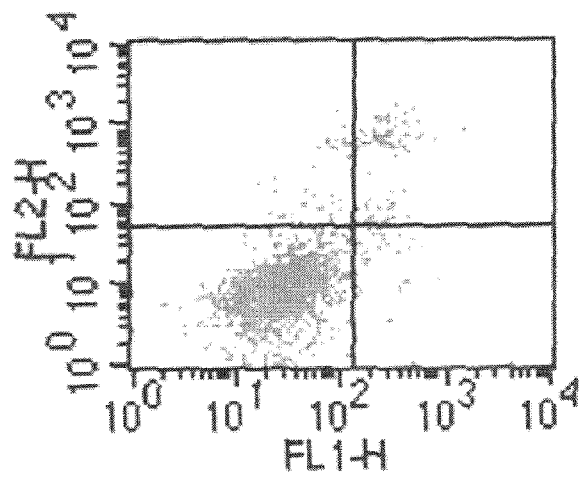
(B)
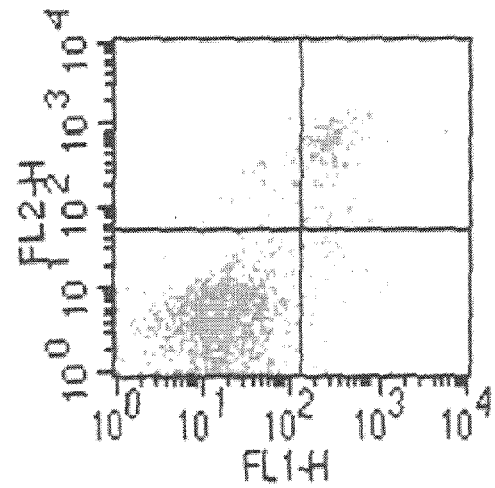
(C)
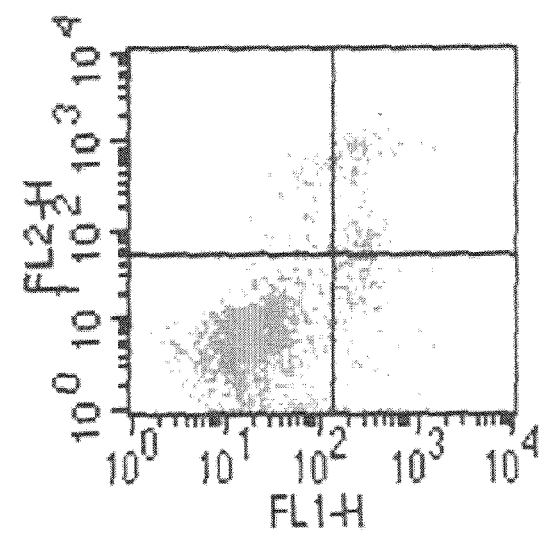
(D)
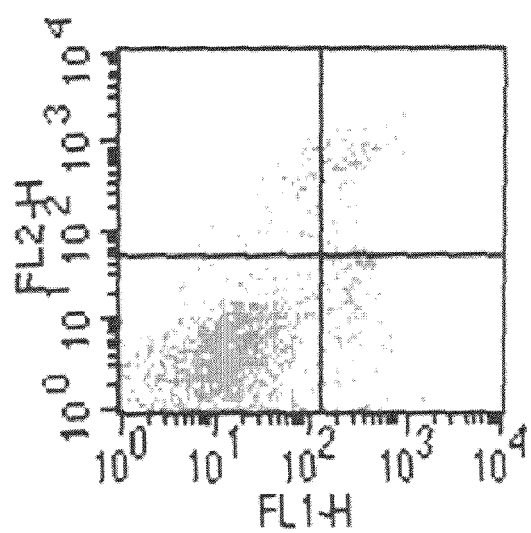

USE OF AGMATINE FOR PROTECTION OF RETINAL GANGLION CELLS

PRIORITY

This application claims priority under 35 U.S.C. §371 to an international application filed on Apr. 3, 2008 and assigned international application No. PCT/KR2008/001879, which claims priority to an application filed on Apr. 4, 2007 and assigned Korean Patent Application No. 10-2007-0033367, the contents of which are incorporated herein by reference.

TECHNICAL FIELD

The present invention relates to a use method of agmatine or a pharmaceutically allowable salt thereof, and a pharmaceutical composition comprising the same. The method and pharmaceutical composition of the present invention can prevent apoptosis in a Retinal Ganglion Cell (RGC), particularly apoptosis induced by hypoxia or Tumor Necrosis Factor-alpha (TNF-α). Also, the method and pharmaceutical composition of the present invention can effectively cure or prevent eye diseases, preferably including glaucoma, retinopathy, and optic neuropathy.

BACKGROUND ART

Glaucoma is the second leading cause of unrecoverable blindness, and globally there are about 5 million patients who had lost their vision due to glaucoma, which are about 12.3% of global blindness (Foster and Resnikoff, 2005; and Resnikoff et al., 2002). Glaucoma is not a single disease, but rather represents a group of diseases of various patterns that show diverse clinical and histopathologic manifestations, such as certain changes in the optic disc and damages to RGCs with resultant visual field loss. Although there are other various diseases besides glaucoma that lead to RGC injury, selective and progressive death of RGCs is a distinctive feature of glaucoma (Osborne et al. 1999; Kaushik et al., 2003; and Kuehn et al., 2005). Therefore, a major goal of glaucoma therapy is to prevent the death of RGCs.

It is a well-known fact that a rise of IntraOcular Pressure (IOP) is the most definite risk factor among others associated with glaucoma, and lowering the IOP to an appropriate level can slow the progression of glaucoma (Chauhan and Drance, 1992; Dielemans et al., 1994; Collaborative Normal-Tension Glaucoma Study Group, 1998a, 1998b; Heijl et al., 2002; and Maier et al., 2005). Based on this fact, glaucoma studies in the last several decades have focused on lowering the IOP. However, it has been reported that glaucomatous damage can continue in some patients even after the IOP has been lowered to a proper level, and this phenomenon was observed even in some glaucoma patients whose IOP is within the normal range (Werner and Drance, 1977). These facts imply that there are another mechanisms related to the development and progression of glaucoma, in addition to the elevation of IOP. Therefore, many glaucoma studies have attempted to find other mechanisms that cause selective RGC apoptosis, which is the most crucial pathophysiologic feature of glaucoma. It was found that hematological factors (e.g., loss of autoregulation in ocular perfusion pressure and hypoxia resulted therefrom, ischemia, ischemic-reperfusion, etc.) are associated with glaucomatous damage (Chung et al., 1999; Cioffi and Wang, 1999; Flammer, 1994; Flammer et al., 2002; and Luo et al., 2001). Recent glaucoma studies have focused to identify neuroprotective effects in prevention of RGC apoptosis (Garcia-Valenzuela et al., 1995; Gross et al., 1999; Quigley et al., 1995; Kerrigan et al., 1997; Okisaka et al., 1997; and Kuehn et al., 2005).

It is well-known that TNF-α, which is a proinflammatory cytokine that is synthesized and released from astrocytes and microglia in the Central Nervous System (CNS), is implicated in cytotoxicity in several neurodegenerative diseases including multiple sclerosis, Parkinson's disease, and Alzheimer's disease (Moreau et al., 1996; Tarkowski et al., 2003; and Sawada et al., 2006). Such cell cytotoxicity of TNF-α is caused by cell apoptosis induction through TNF Receptor-1 (TNF-R1) (Hsu et al., 1995). It is reported that TNF-α is also associated with retinal damage or optic nerve damage in retinal tissue induced by ischemia (Fontaine et al., 2002; Gardiner et al., 2005; Koizumi et al., 2003; and Yoshida et al., 2004). This implies that TNF-α induced neuro-retinal apoptosis is involved in pathologic damage due to a mechanism related to ischemic retinopathy and ischemic neuropathy. Moreover, the fact that TNF-α induced by optic nerve damage from axotomy or crushing damage is the cause of RGC death means that TNF-α is associated with neuro-retinal injury by traumatic optic neuropathy as well (Diem et al., 2001; and Tezel et al., 2004). It is also known that TNF-α is involved in AIDS-related optic neuropathy (Lin et al., 1997).

Particularly, it is reported that TNF-α and its receptor TNF-R1 are upregulated in patients with glaucoma. TNF-α is upregulated in glial cells of glaucoma patients and TNF-R1 is upregulated in RGCs (Tezel et al., 2001). Microgliacytes and astrocytes of glaucomatous optic nerve heads contain abundant TNF-α (Yan et al., 2000; Yuan and Neufeld, 2000, 2001). In an in vitro glaucoma experimental model of ischemia or with an elevated hydrostatic pressure, TNF-α production is increased in glial cells, which induces apoptosis in RGCs (Agar et al., 2006; and Tezel et al., 2000). A similar result may also be obtained in an in vivo glaucoma animal test that intravitreal injection of TNF-α induces axonal degeneration and delayed loss of RGC cell bodies (Kitaoka et al., 2006). Intravitreal injection of TNF-α to rabbit eyes induces degeneration of optic nerves (Madigan et al., 1996). Until now, there has been no evidence that TNF-α directly contributes to RGC death, but it is considered that, according to previous reports, TNF-α would play a critical role in the pathogenesis of RGC apoptosis in glaucomatous eyes.

From the late 1990's, researchers have been actively seeking for drugs having neuroprotective effects against RGC death due to glaucoma. It is reported that calcium channel blockers (Kitazawa et al., 1989; Netland et al., 1993; Bose et al., 1995; and Sawada et al., 1996), neurotrophines (Johnson et al., 1986; Mansour-Robaey et al., 1994; Weibel et al., 1995; Di Polo et al., 1998; Pease et al., 2000; Quigley et al., 2000; Ko et al., 2001; Martin et al., 2003; and Ji et al., 2004), $α_2$-adrenergic agonists (Donello et al., 2001; Lafuente et al., 2001, 2002; WoldeMussie et al., 2001; Aviles-Trigueros et al., 2003; and Wheeler et al., 2003), N-Methyl-D-Aspartate (NMDA) receptor antagonists (Vorwerk et al., 1996; and Hare et al., 2004a, b), Nitric Oxide Synthase (NOS) inhibitors (Neufeld et al., 2002), and other materials (Chaudhary et al., 1999; Kipnis et al., 2000; Schori et al., 2001; Quaranta et al., 2003; Hirooka et al., 2004; Qin et al., 2004; and Lingor et al., 2005) have neuroprotective effects on RGCs. However, an accurate mechanism for RGC apoptosis induced by glaucoma is not yet known, and an effective neuroprotective drug for the inhibition of apoptosis of RGCs has not been developed to date.

DISCLOSURE

Technical Problem

Meanwhile, in recent various in vitro and in vivo cerebral injury experimental models, it has been demonstrated that agmatine has neuroprotective effects. It is also known that agmatine reduces the infarct area and neuronal loss in cerebral ischemic and ischemic-reperfusion injury models (Gilad et al., 1996; Kim et al., 2004; and Kim et al., 2006). In addition, it is known that agmatine protects neurons from apoptosis after exposure to NMDA and glutamate (Olmos et al., 1999; Zhu et al., 2003; and Wang et al., 2006). Its protective effects are also shown in neuronal loss after exposure to steroid or MPTP (Gilad et al., 2005; and Zhu et al., 2006). Neuroprotective effects of agmatine were proved not only in cerebral injury models but also spinal cord injury models (Gilad and Gilad, 2000; Yu et al., 2000, 2003; and Kotil et al., 2006). However, protective effects of agmatine on RGCs that may be achieved by reducing apoptosis of RGCs have never been discussed or reported. In addition, agmatine has a role as an $\alpha_2$-adrenergic agonist, and thus, can suppress RGC death by neuroprotective mechanisms and also protect RGCs by lowering the IOP (Gabelt et al., 1994; Greenfield et al., 1997; Li et al., 1994; and Toris et al., 1995), but this fact has not been discussed or reported up to now.

Technical Solution

It is, therefore, the primary object of the present invention to provide a method and pharmaceutical composition for curing or preventing associated eye diseases by protecting RGCs from apoptosis with help of agmatine or a pharmaceutically allowable salt thereof.

ADVANTAGEOUS EFFECT

The present inventors confirmed that agmatine, an endogenous polyamine with a guanidino group, prevents hypoxia-induced increase in Lactate DeHydrogenase (LDH) release and apoptotic death of RGCs, and TNF-$\alpha$ induces LDH release and apoptosis of RGCs. Further, the present inventors found that agmatine can suppress the cytotoxic effects of TNF-$\alpha$ on RGCs. By doing this, the present inventors provide agmatine as a medicine for curing or preventing eye diseases related to apoptosis of RGCs.

DESCRIPTION OF DRAWINGS

FIG. 1 illustrates LDH release in transformed RGC (RGC-5), comparing the neuroprotective effects of agmatine and Brain-Derived Neurotrophic Factor (BDNF) against hypoxia for 12 hours (A), 24 hours (B), and 48 hours (C), in which resultant data are shown as mean±S.E.M. of 32 measurements (*P<0.001);

FIG. 2 shows pictures (magnification: X400) to illustrate progressive reduction of the hypoxia-induced cell death in RGC-5 in the presence of agmatine and/or BDNF, the RGCs being exposed to hypoxia for 48 hours either alone (B) or in the presence of agmatine (100 μM) (C) or BDNF (10 ng/mL) (D) in comparison with a control normoxic culture shown in (A), in which the cultures are stained with Hoechst 33342 and Propidium Iodide (PI);

FIG. 3 shows flow cytometric analysis results on the protective effects of agmatine and BDNF on the hypoxia-induced apoptosis of RGC-5, the RGCs being exposed to hypoxia for 12 hours either alone (B) or in the presence of agmatine (100 μM) (C) or BDNF (10 ng/ml) (D) in comparison with a control normoxic culture shown in (A), in which the cultures are stained with annexin-V-FITC and P I and the cells of high reactivity with FITC and low reactivity with PI (right lower side) are early apoptotic cells;

FIG. 4 shows flow cytometric analysis results on the protective effects of agmatine and BDNF on the hypoxia-induced apoptosis of RGC-5, the RGCs being exposed to hypoxia for 24 hours either alone (B) or in the presence of agmatine (100 μM) (C) or BDNF (10 ng/ml) (D) in comparison with a control normoxic culture shown in (A), in which the cultures are stained with annexin-V-FITC and P I and the cells of high reactivity with FITC and low reactivity with PI (right lower side) are early apoptotic cells;

FIG. 5 illustrates a colorimetric analysis result on the protective effects of agmatine on the caspase-3 activity induced by hypoxia in RGC-5, the RGCs being exposed to hypoxia for 24 hours with or without agmatine (100 μM) or Z-VAD-FMK (50 μM), in which specific activity of caspase-3 is measured by cleavage of the caspase-3 substrate (Ac-DEVD-pNA);

FIG. 6 illustrates a western blot analysis result of the protective effects of agmatine and BDNF on Mitogen-Activated Protein Kinases (MAPKs), in which western immunoblots are probed with antibodies against c-Jun N-terminal Kinase (JNK) and phospho-JNK (A), Extracellular signal-Regulated Kinase (ERK) and phospho-ERK (B), phospho-p38 kinase (p38) and phospho-p38 (C), and β-actin (D);

FIG. 7 illustrates a western blot analysis result on the protective effects of agmatine and BDNF on Nuclear Factor-Kappa B (NF-κb), in which western immunoblots are probed with antibodies against NF-κB and phospho-NF-κB from nuclear (A) and cytosolic (B) proteins, and histone 3(A) and β-actin (B) are used as internal controls;

FIG. 8 compares the neuroprotective effects of agmatine and BDNF on LDH release in RGC-5 cell death induced by the exposure to TNF-$\alpha$ for 24 hours (A) and 48 hours (B), in which data are shown as mean±S.E.M. of 32 measurements (*P<0.001);

FIG. 9 shows pictures (magnification: X400) to illustrate progressive reduction of the TNF-$\alpha$-induced cell death in RGC-5 in the presence of agmatine, the RGCs being exposed to TNF-$\alpha$ for 48 hours either alone (C) or in the presence of agmatine (100 μM) (D) in comparison with a control culture shown in (A) and a culture with an additional 100 μM of agmatine shown in (B), in which the cultures are stained with Hoechst 33342 and PI;

FIG. 10 shows flow cytometric analysis results on the protective effects of agmatine on the apoptosis of RGC-5 induced by TNF-$\alpha$, the RGCs being exposed to 50 ng/mL of TNF-$\alpha$ for 12 hours without agmatine (C) or in the presence of agmatine (100 μM) (D) in comparison with a control normoxic culture shown in (A) and a culture with an additional 100 μM of agmatine shown in (B), in which the cultures are stained with annexin-V-FITC and PI, and the cells having a high reactivity with FITC and low reactivity with PI (right lower side) are early apoptotic cells; and FIG. 11 shows flow cytometric analysis results on the protective effects of agmatine on the apoptosis of RGC-5 induced by TNF-$\alpha$, the RGCs being exposed to 50 ng/mL of TNF-$\alpha$ for 24 hours alone (C) or in the presence of agmatine (100 μM) (D) in comparison with a control normoxic culture shown in (A) and a culture with an additional 100 μM of agmatine shown in (B), in which the cultures are stained with annexin-V-FITC and PI, and the cells having a high reactivity with FITC and low reactivity with PI (right lower side) are early apoptotic cells.

BEST MODE

In accordance with one aspect of the present invention, there is provided a novel method for preventing apoptosis of mammalian RGCs by using agmatine or pharmaceutically allowable salts thereof.

In accordance with another aspect of the present invention, there is provided a composition comprising agmatine or pharmaceutically allowable salts thereof to prevent apoptosis of mammalian RGCs.

In accordance with still another aspect of the present invention, there is provided a novel method for curing or preventing eye diseases related to apoptosis of mammalian RGCs by using a therapeutically effective dose of agmatine or pharmaceutically allowable salts thereof.

In accordance with yet another aspect of the present invention, there is provided a pharmaceutical composition comprising a therapeutically effective dose of agmatine or pharmaceutically allowable salts thereof as an active ingredient to cure or prevent eye diseases related to apoptosis of mammalian RGCs.

Hereinafter, exemplary embodiments of the present invention will be described in detail with reference to the accompanying drawings.

MODE FOR INVENTION

In the present invention, agmatine is an endogenous polyamine that is synthesized from the decarboxylation of L-arginine by mitochondrial arginine decarboxylase (Tabor and Tabor, 1984; Reis and Regunathan, 2000; Grillo and Colombatto, 2004; and Moinard et al., 2005). Also, agmatine is widely and unevenly expressed in the brain and other tissues of mammals (Li et al., 1994; and Lortie et al., 1996), and is formed in situ and from exogenous sources (Grillo and Colombatto, 2004; and Moinard et al., 2005). Further, agmatine has been reported to have various biological actions; and it stimulates release of catecholamines from adrenal chromaffin cells (Li et al., 1994), insulin from pancreatic islets (Sener et al., 1989), and luteinizing hormone-releasing hormone from the hypothalamus (Kalra et al., 1995). In addition, agmatine enhances the analgesic effect of morphine (Kolesnikov et al., 1996; and Su et al., 2003), inhibits the activity of inducible NOS (Galea et al., 1996), and contributes to polyamine homeostasis (Dudkowska et al., 2003; and Grillo and Colombatto, 2004). Also, agmatine is known as an agonist for $\alpha_2$-adrenergic and imidazoline receptors (Li et al., 1994), and an antagonist for an NMDA receptor (Yang and Reis, 1999). Further, agmatine may be produced by a well-known enzymatic or chemical synthesis method in the art to which the present invention pertains, or available from a specific source. Moreover, agmatine herein implies agmatine itself as well as pharmaceutically allowable salts thereof.

In the present invention, RGC apoptosis is preferably hypoxia-induced apoptosis or TNF-$\alpha$ induced apoptosis.

In the present invention, eye diseases related to RGC apoptosis include, but are not limited to, glaucoma, retinopathy, and optic neuropathy. More preferably, eye diseases herein include glaucoma, ischemic retinopathy, ischemic neuropathy, traumatic optic neuropathy, and AIDS-related optic neuropathy.

In the present invention, mammal is preferably a human.

The composition used in the present invention may be selected from diverse forms of pharmaceutical compositions. Preferably, the composition is a local ophthalmic preparation to be transferred to eyes. The composition may contain an ophthalmically acceptable preservative, viscosity enhancer, penetration enhancer, buffer, sodium chloride, and water to form an aqueous, sterile ophthalmic suspension or solution. The ophthalmic solution can be prepared by dissolving its active ingredient in a physiologically acceptable isotonic aqueous buffer solution. Also, the ophthalmic solution may contain an ophthalmically acceptable surfactant to facilitate the dissolution of the active ingredient. Further, the ophthalmic solution may contain an enhancer or a gelling agent.

A specific dose of the composition for an individual used in the present invention is up to the clinician. Needless to say, a dose may vary depending on disease severity, age, and weight of a patient. The active ingredient, i.e. agmatine, will be typically contained in the amount of about 0.1-1.0% by weight, preferably about 0.1-0.5% by weight, and most preferably about 0.2% by weight of the composition or the preparation.

The composition of the present invention can be delivered to an eye by a conventional technique well-known to a person skilled in the art, for example, in the form of a local eyedrop or ointment, or with the help of a sustained-releasing device provided in an eye; by injection such as intravitreal, subconjunctival, or subtenon injection, or general injection such as oral, intravenous, hypodermical, or intramuscular injection; or by parenteral administration, intradermal administration or intranasal administration.

Hereinafter, the present invention will be described in more detail.

The present inventors hypothesized that agmatine may protect RGCs because of its role as an $\alpha_2$-adrenergic agonist (Li et al., 1994), an NMDA receptor antagonist (Yang and Reis, 1999), and a suppressor of inducible NOS (Galea et al., 1996). In the present invention, the present inventors studied the neuroprotective effect of agmatine on TNF-$\alpha$ induced apoptosis of transformed rat's RGCs (RGC-5) (Krishnamoorthy et al., 2001; and Maher and Hanneken, 2005). In addition, the neuroprotective effect of agmatine on hypoxia-induced apoptosis of RGCs was studied. Then, the neuroprotective effect of agmatine was compared to that of BDNF, which is a well-known protective neurotrophin for RGCs. The present inventors proved the fact that agmatine has a neuroprotective effect on TNF-$\alpha$ induced apoptosis in RGCs, and also confirmed that agmatine protects RGCs from hypoxia-induced cell damage and its neuroprotective effect is much more powerful than that of BDNF which is a well-known protective neurotrophin for RGCs. The neuroprotective effect of agmatine is associated with JNK and NF-$\kappa$B signaling pathways, implying that agmatine uses a different mechanism from BDNF. These study results suggest that agmatine may become the basis of a novel therapeutic strategy for eye diseases related to RGC injury.

The following examples are provided to explain the present invention in more detail, but it should be noted that the present invention is not limited thereto.

EXAMPLES

Example 1

Protective Effect of Agmatine on RGCS from Hypoxia-Induced Apoptosis 1.1. Chemicals and Antibodies Agmatine sulfate (Cat no. A7127) and recombinant human BDNF (Cat no. 248-BD-025) were purchased from Sigma and R&D System, respectively. Rabbit polyclonal anti-JNK p54/46 (Cat no. 9252), anti-ERK p44/42 (Cat no. 9102), anti-p38 (Cat no. 9212), anti-NF-$\kappa$B p65 (Cat no. 3034), anti-phospho-JNK p54/46 (Cat no. 9251), anti-phospho-ERK p44/42 (Cat no. 9101), anti-phospho-p38 (Cat no. 9211), anti-phospho-NF-$\kappa$B p65 (Cat no. 3031), and anti-histone 3 (Cat no. 9715) antibodies were purchased from Cell Signaling Technology. Mouse monoclonal anti-β-actin antibody (Cat no. sc-47778) was purchased from Santa Cruz Biotechnology, Inc.

1.2. Cell Culture

The RGC-5 cell line, which is a RGC line developed from post-natal Sprague-Dawley rats, was grown in modified Dulbecco's Modified Eagle's Medium (DMEM; Gibco) supplemented with 10% of heat inactivated fetal bovine serum (Gibco) and 100 U/mL of penicillin and 100 µg/mL of streptomycin (Gibco). The cells were passaged every 2 to 3 days, and the cultures incubated at 37° C. in 5% of $CO_2$ and air. During cultivation, the cells exhibited the same morphological phenotype. For all experiments, cells were used at an 80% confluence.

1.3. Hypoxic Injury to RGCs

Cultures were transferred into a closed hypoxic chamber (Form a Scientific Co.) in which oxygen level (5% of $O_2$, 5% of $CO_2$, 90% of $N_2$) and temperature (37° C.) were controlled. After washing twice with deoxygenated serum-free DMEM, cells were maintained in the hypoxic chamber. Control cells were not exposed to hypoxia. Agmatine or BDNF were added to the culture medium at the start of injury as indicated.

1.4. LDH Assay

Cell viability was quantified by measurement of LDH released by injured cells after hypoxic or normoxic culture for 12, 24, and 48 hours. LDH release is expressed as a value relative to the value of 100, which represents the maximum LDH release that occurred after freezing of each culture at −70° C. overnight and rapid thawing, which induces nearly complete cell damage. All experiments were performed in at least quadruplicate and repeated at least eight times using cell cultures derived from different platings. The preliminary studies with the LDH assay tested agmatine concentrations from 10 µM to 1 mM and BDNF concentrations from 5 ng/mL to 100 ng/mL. Cell death was reduced significantly at 100 µM and greater concentrations of agmatine and 10 ng/mL and greater concentrations of BDNF, so the present inventors used 100 µM of agmatine and 10 ng/mL of BDNF for subsequent experiments.

1.5. Hoechst 33342 and PI Staining

Apoptotic or necrotic cell death was characterized by the use of Hoechst 33342 and PI double staining. Cells were stained with 10 µg/mL of Hoechst 33342 and 10 µg/mL of PI at 37° C. for 30 minutes. After washing twice with phosphate buffered saline (PBS), cells were imaged with a digital camera attached to a fluorescence microscope.

1.6. Annexin-V Assay

The percentage of cells actively undergoing apoptosis was determined by flow cytometry using the Annexin V-FITC Apoptosis Detection Kit (BD Biosciences, Cat no. 556547) according to the manufacturer's instructions. Briefly, cells were harvested and resuspended in binding buffer ($10^6$ cells/mL). $10^5$ cells were mixed with 5 µL of annexin V-FITC and 5 µL of PI. After incubating at room temperature for 15 minutes in the dark, analysis was performed by flow cytometry.

1.7. Measurement of Caspase-3 Activity

Caspase-3 activity was measured using the CaspACE™ colorimetric assay system (Promega, Cat no. G7220) according to the manufacturer's instructions. Briefly, cells were harvested and resuspended in cell lysis buffer ($10^8$ cells/mL). After lysis, $10^6$ cells were mixed with 32 µL of assay buffer and 2 µL of 10 mM DEVD-pNA substrate. After incubating at 37° C. for 4 hours, absorbance was measured using a microplate reader at 405 nm. Absorbance of each sample was determined by subtraction of the mean absorbance of the blank from that of each sample.

1.8. Western Blot Analysis

For extraction of whole cellular proteins, cells were washed twice with ice-cold PBS and then lysed with cell lysis buffer (50 mM of Tris-HCl (pH 7.4), 1% of NP-40, 0.25% of Na-deoxycholate, 150 mM of NaCl, 1 mM of EDTA, 10 mM of $Na_3VO_4$, 50 mM of NaF, 1 mM of PMSF, 1 µg/mL of aprotinin, 1 µg/mL of leupeptin, 1 µg/mL of pepstatin) on ice for 30 minutes. Lysates were sonicated, and the cell homogenates were centrifuged at 15,000 g at 4° C. for 10 minutes.

For fraction of cytosolic and nuclear proteins, cells were lysed with lysis buffer A (10 mM of HEPES (pH 7.4), 10 mM of KCl, 0.1 mM of EDTA, 0.1 mM of EGTA, 1 mM of DTT, 10 mM of $Na_3VO_4$, 50 mM of NaF, 1 mM of PMSF, 1 µg/mL of aprotinin, 1 µg/mL of leupeptin, 1 µg/mL of pepstatin) on ice for 15 minutes, and 10% of NP-40 was then added thereto. After vortexing for 10 seconds, lysates were centrifuged at 15,000 g at 4° C. for 1 minute. The supernatent was collected from the cytosolic fraction. The pellet was resuspended in lysis buffer C (20 mM of HEPES (pH 7.4), 400 mM of NaCl, 1 mM of EDTA, 1% of glycerol, 1 mM of DTT, 10 mM of $Na_3VO_4$, 50 mM of NaF, 1 mM of PMSF, 1 µg/mL of aprotinin, 1 µg/mL of leupeptin, 1 µg/mL of pepstatin) on ice for 30 minutes. Lysates were centrifuge at 15,000 g at 4° C. for 15 minutes. The supernatant was collected from the nuclear fraction.

The protein concentrations in the resultant supernatants were measured with the Bradford reagent, and equal amounts of protein (40 µg) were boiled in Laemmli sample buffer, followed by being resolved by 10 or 15% SDS-PAGE. The proteins were transferred to polyvinylidene fluoride membranes (Immobilon; Millipore, Billerica, Mass.) and then probed overnight with antibodies against JNK, ERK p44/42, p38, NF-κB p65, phospho-JNK, phospho-ERK p44/42, phospho-p38, phospho-NF-κB, β-actin and histone 3 as indicated (diluted 1:1000). The immunoreactive bands were detected with horseradish peroxidase-conjugated secondary antibodies and visualized by enhanced chemiluminescence.

1.9. Statistical Analysis

Experimental results were analyzed by 2-tailed Student t-test or one-way ANOVA using the Statistical Package for Social Sciences 12.0 (SPSS). Differences were considered statistically significant at $p<0.05$.

1.10. Results

Agmatine Inhibits Hypoxia-Induced Cell Death of RGC-5

The present inventors first examined the effect of hypoxia on cultured transformed rat RGCs (RGC-5). As shown in FIG. 1, the effects of hypoxic conditions on RGCs were significant (all $P<0.001$). Exposure to hypoxia for 12, 24, and 48 hours significantly increased LDH release by 10.17%, 20.04%, and 52.25%, respectively. This result indicates a hypoxia-induced time-dependent neurotoxicity on RGCs.

Next, the present inventors examined possible neuroprotective effects of agmatine on hypoxia-induced RGC damage, and compared these effects to those of BDNF. The results indicate a significant influence of agmatine on hypoxic neuronal damage, and this effect was much more powerful than that observed for BDNF. After exposure to hypoxia for 12 and 24 hours (see FIGS. 1(A) and 1(B)), none of the treatment groups showed a significant effect on the increased LDH release induced by hypoxia (P=0.864 and P=0.266, respectively). As illustrated in FIG. 1(C), however, there were significant effects of agmatine and BDNF on LDH release (all $P<0.001$). 100 µM and 500 µM of agmatine prevented the hypoxia-induced increase of LDH release to 25.60% and 27.09%. Similarly, 10, 50, and 100 ng/mL of BDNF inhibited the release of LDH to 30.10%, 33.67%, and 36.06%, respectively. In addition, 100 μM of agmatine was more effective in suppressing LDH release than 10 ng/mL BDNF (P<0.001).

The neuroprotective effects of agmatine were further studied using Hoechst 33342 and PI double staining. After 48 hours, the control normoxic culture exhibited confluent Hoechst-positive cells with homogeneous and compact nuclear morphology, and sparse numbers of PI-labeled cells (see FIG. 2(A)). Exposure of cultures to hypoxia for 48 hours resulted in a significant loss of Hoechst-positive cells and the appearance of many PI-positive cells with distorted and condensed nuclei (see FIG. 2(B)). The RGC loss was prevented by the addition of 100 μM of agmatine (see FIG. 2(C)) or 10 ng/mL of BDNF (see FIG. 2(D)) to the cultures.

Agmatine Protects RGC-5 from Hypoxia-induced Apoptosis

In order to verify whether agmatine has protective effects on the hypoxia-induced apoptotic death of RGCs, the present inventors tested these cells using an annexin-V assay. While there was no significant difference in the proportion of apoptotic cells after exposure to hypoxia for 12 hours (see FIG. 3), there was a significant decrease in apoptotic cells in the presence of agmatine or BDNF after exposure to hypoxia for 24 hours (see FIG. 4).

Using the caspase-3 assay, the present inventors studied whether agmatine has an effect on the hypoxia-induced specific activity of caspase-3. The specific activity of caspase-3 was measured by cleavage of the caspase-3 substrate (Ac-DEVD-pNA). After 24 hours of hypoxia, there was a significant induction of caspase-3 activity, which was equally suppressed by treatment with 100 μM of agmatine or 50 μM of caspase-3 inhibitor Z-VAD-FMK (see FIG. 5).

Selective Suppression of JNK Activation by Agmatine

Representative Western blots of the total and phosphorylated MAPKs, and β-actin of RGCs after hypoxic injury are shown in FIG. 6.

The antibody against phospho-JNK detected two bands at 54 and 46 kDa, and both bands showed similar changes in this study. Increases of phospho-JNKs in hypoxic RGCs became evident 9 hours after hypoxic injury and remained elevated (see FIG. 6(A)). Treatment with Agmatine, but not BDNF, significantly suppressed hypoxia-induced expression of phospho-JNKs.

The antibody against the phospho-ERK also detected two bands at 44 and 42 kDa, and both bands showed a similar trend in this study. Phospho-ERKs were not detected in normoxic cultures of RGCs, but were highly expressed in RGCs after exposure to hypoxia for 3 hours and remained elevated (see FIG. 6(B)). Treatment with BDNF completely blocked the expression of phospho-ERKs after exposure to hypoxia for 3 and 6 hours, but had no effect thereafter. In comparison, agmatine did not significantly affect the expression of phospho-ERKs.

The antibody against p38 detected one band at 38 kDa. Phospho-p38 was not detected in normoxic RGCs until after 12 hours, but was evident in hypoxic RGCs after exposure to hypoxia for 3 hours and remained elevated (see FIG. 6(C)). BDNF only blocked the expression of phospho-p38 at 6 hours and agmatine had no effect on phospho-p38 levels.

Total MAPKs (JNK, ERK, and p38) and β-actin were unaffected by hypoxic injury (see FIG. 6). There were no significant changes after treatment with BDNF or agmatine.

Thus, phospho-MAPKs showed different activation profiles after exposure to hypoxia; and ERK and p38 were initially activated, and JNK was activated later. BDNF inhibited the activation of ERK (at 3 and 6 hours after exposure to hypoxia) and p38 (at 6 hours after exposure to hypoxia), while agmatine suppressed the activation of JNK (with a significant increase at 9 hours after exposure to hypoxia).

Suppression of NF-κB Signaling by Agmatine

The expression and activation of the NF-κB were evaluated from the nuclear and cytosolic fraction of RGCs after hypoxic injury. The representative bands in Western blot analysis are shown in FIG. 7. The antibodies against total and phospho-NF-κB detected their representative bands at 65 kDa.

In the nuclear fraction, total NF-κB and histone 3 were unaffected by hypoxic injury, and there were no significant changes with the addition of BDNF and agmatine. However, the phospho-NF-κB was significantly increased in RGCs by hypoxia after 1 hour and returned to normal levels after 3 hours. The increase in phospho-NF-κB was suppressed by agmatine, but not BDNF, treatment.

On the other hand, in the cytoplasmic fraction there were no significant changes in levels of phospho-NF-κB and β-actin in hypoxic RGCs. However, total NF-κB expression increased after exposure to hypoxia for 1 hour and returned to normal levels after 3 hours. This increase was inhibited by treatment with agmatine, but not BDNF.

Example 2

Protective Effect of Agmatine on RGCs from TNF-α-Induced Apoptosis 2.1. RGC-5 Culture and Exposure to TNF-α

The RGC-5 cell line, which is an RGC line developed from post-natal Sprague-Dawley rats, was grown in modified DMEM (Gibco) supplemented with 10% of heat inactivated fetal bovine serum (Gibco) and 100 U/mL of penicillin and 100 μg/mL of streptomycin (Gibco). The cells were passaged every 2 to 3 days and incubated at 37° C. in 5% of $CO_2$ and air. At cultivation, the cells had the same morphology. For all experiments, cells were used at 80% of confluence.

After washing twice with PBS, cells were cultured in serum-free DMEM and treated with either 10 or 50 ng/mL of recombinant rat TNF-α (Chemicon) for up to 48 hours. The control cells were not exposed to TNF-α. 100 μM of agmatine was added to the culture medium at the start of injury as indicated.

2.2. LDH Assay

Cell viability was quantified by measuring the amounts of LDH released from the injured cells after TNF-α administration. LDH release is expressed as a value relative to the value of 100, which is the maximum LDH release that occurs after freezing each culture at −70° C. overnight and then rapidly thawing, thus inducing nearly complete cell damage. All experiments were performed in at least quadruplicate, and repeated at least eight times using cell cultures derived from different platings.

2.3. Hoechst 33342 and PI Staining

Apoptotic or necrotic cell death was characterized by double staining cells with Hoechst 33342 and PI. Cells were stained with 10 μg/mL of Hoechst 33342 and 10 μg/mL of PI at 37° C. for 30 minutes. After being washed twice with PBS, cells were imaged with a digital camera attached to a fluorescence microscope.

2.4. Annexin-V Assay

The percentage of cells actively undergoing apoptosis was determined by flow cytometry using the Annexin V-FITC Apoptosis Detection Kit (BD Biosciences, Cat no. 556547) according to the manufacturer's instructions. Briefly, cells were harvested and resuspended in binding buffer ($10^6$ cells/mL). $10^5$ cells were mixed with 5 μL of annexin V-FITC and 5 μL of PI. After incubating at room temperature for 15 minutes in the dark, analysis was performed by flow cytometry.

2.5. Statistical Analysis

Experimental results were analyzed by 2-tailed Student t-test or one-way ANOVA using the Statistical Package for Social Sciences 12.0 (SPSS). Differences were considered statistically significant at p<0.05.

2.6. Results

Agmatine Inhibits TNF-α-Induced Apoptosis in RGC-5 Cells

The present inventors first examined the effect of TNF-α on RGC-5 cells. As shown in FIG. 8, exposure to TNF-α induced a time-dependent and dose-dependent cellular toxicity in RGC-5 cells. Addition of 10 ng/mL of TNF-α for 24 and 48 hours significantly increased LDH release by 7.04±3.26% and 10.16±1.77%, respectively, and addition of 50 ng/mL of TNF-α for the same amount of time significantly increased LDH release by 13.41±6.20% and 17.00±1.92%, respectively. In the control group, LDH was increased by 5.04±1.45% and 6.11±1.28% at 24 and 48 hours, respectively. The cytotoxic effects of TNF-α on RGCs were significant (all P<0.001).

In the presence of 100 μM of agmatine, the TNF-α-induced LDH release was significantly inhibited (all P<0.001). In the group stimulated with 50 ng/mL of TNF-α, the agmatine significantly reduced the release of LDH by 5.91±0.86% and 8.14±2.43% at 24 hours and 48 hours, respectively (see FIG. 8). Thus, agmatine shows neuroprotective effects in RGCs damaged by TNF-α.

The neuroprotective effects of agmatine were further studied using Hoechst 33342 and PI double staining. After 48 hours, the control culture exhibited confluent Hoechst-positive cells with homogeneous and compact nuclear morphology, and rare PI-labeled cells (see FIG. 9(A)). The addition of only 100 μM of agmatine did not have a significant effect (see FIG. 9(B)). However, exposure of cultures to 50 ng/mL of TNF-α for 48 hours resulted in a significant loss of Hoechst-positive cells and the appearance of many PI-positive cells with distorted and condensed nuclei (see FIG. 9(C)). The RGC loss was prevented by the addition of 100 μM of agmatine to the cultures (see FIG. 9(D)).

Agmatine Protects RGC-5s from TNF-α Induced Apoptosis

In order to verify the ability of agmatine to protect against TNF-α-induced apoptotic death in RGCs, the present inventors used an annexin-V assay. While there was no significant difference in the proportion of apoptotic cells after a 12 hour exposure to 50 ng/mL of TNF-α (see FIG. 10), there was a significant decrease in apoptotic cells in the presence of 100 μM of agmatine after 24 hours of exposure (see FIG. 11).

While the present invention has been described with respect to particular examples, it will be apparent to those skilled in the art that various changes and modifications may be made without departing from the spirit and scope of the invention as defined in the following claims. In other words, it will be apparent to those skilled in the art that particular preparations chemically and structurally associated with each other may be substituted to obtain similar results. All examples disclosed in this specification can be practiced without an excessive number of experiments in view of the disclosure. It is also to be understood that the disclosure is for the purpose of explaining particular examples only, and is not intended to be limiting since the scope of the present invention will be limited only by the appended claims.

REFERENCES

The following are the references recited in the disclosure, all of which are provided for supplementary explanation of examples or details disclosed herein and constitute part of the invention.

Agar A, Li S, Agarwal N, Coroneo M T and Hill M A (2006). Retinal ganglion cell line apoptosis induced by hydrostatic pressure. Brain Res 1086:191-200.

Aviles-Trigueros M, Mayor-Torroglosa S, Garcia-Aviles A, Lafuente M P, Rodríguez M E, Miralles de Imperial J, Villegas-Perez M P and Vidal-Sanz M (2003). Transient ischemia of the retina results in massive degeneration of the retinotectal projection: long-term neuroprotection with brimonidine. Exp Neurol 184:767-777.

Bose S, Piltz J R and Breton M E (1995). Nimodipine, a centrally active calcium antagonist, exerts a beneficial effect on contrast sensitivity in patients with normal-tension glaucoma and in control subjects. Opthalmology 102: 1236-1241.

Chaudhary P, Ahmed F, Quebada P and Sharma S C (1999). Caspase inhibitors block the retinal ganglion cell death following optic nerve transection. Brain Res Mol Brain Res 67:36-45.

Chauhan B C and Drance S M (1992). The relationship between intraocular pressure and visual field progression in glaucoma. Graefes Arch Clin Exp Opthalmol 230:521-526. Chung H S, Harris A, Evans D W, Kagemann L, Garzozi H J and Martin B (1999). Vascular aspects in the pathophysiology of glaucomatous optic neuropathy. Sury Opthalmol 43:543-S50. Cioffi G A and Wang L (1999). Optic nerve blood flow in glaucoma. Semin Opthalmol 14:164-170.

Collaborative Normal-Tension Glaucoma Study Group (1998). Comparison of glaucomatous progression between untreated patients with normal tension glaucoma and patients with therapeutically reduced intraocular pressure: Collaborative Normal-Tension Glaucoma Study Group. Am J Opthalmol 126:487-497.

Collaborative Normal-Tension Glaucoma Study Group (1998). The effectiveness of intraocular pressure reduction in the treatment of normal-tension glaucoma: Collaborative Normal-Tension Glaucoma Study Group. Am J Opthalmol 126:498-505.

Di Polo A, Aigner L J, Dunn R J, Bray G M and Aguayo A J (1998). Prolonged delivery of brain-derived neurotrophic factor by adenovirus-infected Muller cells temporarily rescues injured retinal ganglion cells. Proc Natl Acad Sci USA 95:3978-3983.

Diem R, Meyer R, Weishaupt J H and Bahr M (2001). Reduction of potassium currents and phosphatidylinositol 3-kinase-dependent AKT phosphorylation by tumor necrosis factor-(alpha) rescues axotomized retinal ganglion cells from retrograde cell death in vivo. J Neurosci 21:2058-2066.

Dielemans I, Vingerling J R, Wolfs R C, Hofman A, Grobbee D E and de Jong P T (1994). The prevalence of primary open-angle glaucoma in a population-based study in The Netherlands. The Rotterdam Study. Opthalmology 101: 1851-1855.

Donello J E, Padillo E U, Webster M L, Wheeler L A and Gil D W (2001). alpha(2)-Adrenoceptor agonists inhibit vitreal glutamate and aspartate accumulation and preserve retinal function after transient ischemia. J Pharmacol Exp Ther 296:216-233.

Dudkowska M, Lai J, Gardini G, Stachurska A, Grzelakowska-Sztabert B, Colombatto S and Manteuffel-Cymborowska M (2003). Agmatine modulates the in vivo biosynthesis and interconversion of polyamines and cell proliferation. Biochim Biophys Acta 1619:159-166.

Fontains V, Mohand-Said S, Hanoteau N, Fuchs C, Pfizenmaier K and Eisel U (2002). Neurodegenerative and neuroprotective effects of tumor necrosis factor (TNF) in retinal ischemia: opposite roles of TNF receptor 1 and TNF receptor 2, J Neurosci 22: RC216.

Foster A and Resnikoff S (2005). The impact of Vision 2020 on global blindness. Eye 19:1133-1135.

Flammer J (1994). The vascular concept of glaucoma. Sury Opthalmol 38:S3-S6.

Flammer J, Orgul S, Costa V P, Orzalesi N, Krieglstein G K, Serra L M, Renard J P and Stefansson E (2002). The impact of ocular blood flow in glaucoma. Prog Retinal Eye Res 21:359-393.

Fontaine V, Mohand-Said S, Hanoteau N, Fuchs C, Pfizenmaier K and Eisel U (2002). Neurodegenerative and neuroprotective effects of tumor Necrosis factor (TNF) in retinal ischemia: opposite roles of TNF receptor 1 and TNF receptor 2. J Neurosci 22:RC216.

Gabelt B T, Robinson J C, Hubbard W C, Peterson C M, Debink N, Wadhwa A and Kaufman P L (1994). Apraclonidine and brimonidine effects on anterior ocular and cardiovascular physiology in normal and sympathectomized monkeys. Exp Eye Res 59:633-644.

Galea E, Regunathan S, Eliopoulos V, Feinstein D L and Reis DJ (1996). Inhibition of mammalian nitric oxide synthase by agmatine, an endogenous polyamine formed by decarboxylation of arginine. Biochem J 316:247-249.

Garcia-Valenzuela E, Shareef S, Walsh J and Sharma S C (1995). Programmed cell death of retinal ganglion cells during experimental glaucoma. Exp Eye Res 61:31-44.

Gardiner T A, Gibson D S, de Gooyer T E, de la Cruz V F, McDonald D M and Stitt A W (2005). Inhibition of tumor necrosis factor-alpha improves physiological angiogenesis and reduces pathological neovascularization in ischemic retinopathy. Am J Pathol 166:637-644.

Gilad G M and Gilad V H (2000). Accelerated functional recovery and neuroprotection by agmatine after spinal cord ischemia in rats. Neurosci Lett 296:97-100.

Gilad G M, Gilad V H, Finberg J P and Rabey J M (2005). Neurochemical evidence for agmatine modulation of 1-methyl-4-phenyl-1,2,3,6-tetrahydropyridine (MPTP) neurotoxicity. Neurochem Res 30:713-719.

Gilad G M, Salame K, Rabey J M and Gilad V H (1996). Agmatine treatment is neuroprotective in rodent brain injury models. Life Sci 58:PL41-46.

Greenfield D S, Liebmann J M and Ritch R (1997). Brimonidine: a new alpha2-adrenoreceptor agonist for glaucoma treatment. J Glaucoma 6:250-258.

Grillo M A and Colombatto S (2004). Metabolism and function in animal tissues of agmatine, a biogenic amine formed from arginine. Amino Acids 26:3-8.

Gross R L, Hensley S H, Gao F and Wu S M (1999). Retinal ganglion cell dysfunction induced by hypoxia and glutamate: potential neuroprotective effects of beta-blockers. Sury Opthalmol 43:S162-S170.

Hare W A, WoldeMussie E, Lai R K, Ton H, Ruiz G, Chun T and Wheeler L (2004). Efficacy and safety of memantine treatment for reduction of changes associated with experimental glaucoma in monkey, I: functional measures. Invest. Opthalmol V is Sci 45:2625-2639.

Hare W A, WoldeMussie E, Weinreb R N, Ton H, Ruiz G, Wijono M, Feldmann B, Zangwill L and Wheeler L (2004). Efficacy and safety of memantine treatment for reduction of changes associated with experimental glaucoma in monkey, II: structural measures. Invest Opthalmol V is Sci 45:2640-2651.

Heijl A, Leske M C, Bengtsson B, Hyman L, Bengtsson B and Hussein M; Early Manifest Glaucoma Trial Group (2002). Reduction of intraocular pressure and glaucoma progression: results from the Early Manifest Glaucoma Trial. Arch Opthalmol 120:1268-1279.

Hirooka K, Tokuda M, Miyamoto O, Itano T, Baba T and Shiraga F (2004). The *ginkgo biloba* extract (EGB 761) provides a neuroprotective effect on retinal ganglion cells in a rat model of chronic glaucoma. Curr Eye Res 28:153-157.

Hsu H, Xiong J, Goeddel, D V (1995), The TNF receptor 1-associated protein TRADD signals cell death and NF-kappa B activation, Cell 81: 495-504.

Ji J Z, Elyaman W, Yip H K, Lee V W, Yick L W, Hugon J and So KF (2004). CNTF promotes survival of retinal ganglion cells after induction of ocular hypertension in rats: the possible involvement of STAT3 pathway. Eur J Neurosci 19:265-272.

Johnson J E, Barde Y A, Schwab M and Thoenen H (1986). Brain-derived neurotrophic factor supports the survival of cultured rat retinal ganglion cells. J Neurosci 6:3031-3038.

Kalra S P, Pearson E, Sahu A and Kalra P S (1995). Agmatine, a novel hypothalamic amine, stimulates pituitary luteinizing hormone release in vivo and hypothalamic luteinizing hormone-releasing hormone release in vitro. Neurosci Lett 194:165-168.

Kaushik S, Pandav S S and Ram J (2003). Neuroprotection in glaucoma. J Postgrad Med 49:90-95.

Kerrigan L A, Zack D J, Quigley H A, Smith S D and Pease M E (1997). TUNEL-positive ganglion cells in human primary open-angle glaucoma. Arch Opthalmol 115:1031-1035. Kim D J, Kim D I, Lee S K, Suh S H, Lee Y J, Kim J, Chung T S and Lee J E (2006). Protective effect of agmatine on a reperfusion model after transient cerebral ischemia: Temporal evolution on perfusion MR imaging and histopathologic findings. AJNR Am J Neuroradiol 27:780-785. Kim J H, Yenari M A, Giffard R G, Cho S W, Park K A, and Lee JE (2004). Agmatine reduces infarct area in a mouse model of transient focal cerebral ischemia and protects cultured neurons from ischemia-like injury. Exp Neurol 189:122-130.

Kipnis J, Yoles E, Porat Z, Cohen A, Mor F, Sela M, Cohen IR and Schwartz M (2000). T cell immunity to copolymer 1 confers neuroprotection on the damaged optic nerve: possible therapy for optic neuropathies. Proc Natl Acad Sci USA 97:7446-7451.

Kitaoka Y, Kitaoka Y, Kwong J M, Ross-Cisneros F N, Wang J, Tsai R K, Sadun A A and Lam T T (2006). TNF-alpha-induced optic nerve degeneration and nuclear factorkappaB p65. Invest Opthalmol V is Sci 47:1448-1457.

Kitazawa Y, Shirai H and Go F J (1989). The effect of Ca2(+)-antagonist on visual field in low-tension glaucoma. Graefes Arch Clin Exp Opthalmol 227:408-412.

Ko M L, Hu D N, Ritch R, Sharma S C and Chen C F (2001). Patterns of retinal ganglion cell survival after brain-derived neurotrophic factor administration in hypertensive eyes of rats. Neurosci Lett 305:139-142.

Koizumi K, Poulaki V, Doehmen S, Welsandt G, Radetzky S, Lappas A, Kociok N, Kirchhof B and Joussen A M (2003). Contribution of TNF-alpha to leukocyte adhesion, vascular leakage, and apoptotic cell death in endotoxin-induced uveitis in vivo. Invest Opthalmol V is Sci 44:2184-2191.

Kolesnikov Y, Jain S and Pasternak G W (1996). Modulation of opioid analgesia by agmatine. Eur J Pharmacol 296:17-22.

Kotil K, Kuscuoglu U, Kirali M, Uzun H, Akcetin M and Bilge T (2006). Investigation of the dose-dependent neuroprotective effects of agmatine in experimental spinal cord injury: a prospective randomized and placebo-control trial. J Neurosurg Spine 4:392-399.

Krishnamoorthy R R, Agarwal P, Prasanna G, Vopat K, Lambert W, Sheedlo H J, Pang I H, Shade D, Wordinger R J, Yorio T, Clark A F and Agarwal N (2001). Characterization of a transformed rat retinal ganglion cell line. Brain Res Mol Brain Res 86:1-12.

Kuehn M H, Fingert J H and Kwon Y H (2005). Retinal ganglion cell death in glaucoma: mechanisms and neuroprotective strategies. Opthalmol Clin North Am 18:383-395, vi.

Lafuente M P, Villegas-Perez M P, Mayor S, Aguilera M E, Miralles de Imperial J and Vidal-Sanz M (2002). Neuroprotective effects of brimonidine against transient ischemia-induced retinal ganglion cell death: a dose response in vivo study. Exp Eye Res 74:181-189.

Lafuente M P, Villegas-Perez M P, Sobrado-Calvo P, Garcia-Aviles A, Miralles de Imperial J and Vidal-Sanz M (2001). Neuroprotective effects of alpha(2)-selective adrenergic agonists against ischemia-induced retinal ganglion cell death. Invest Opthalmol V is Sci 42:2074-2084.

Li G, Regunathan S, Barrow C J, Eshraghi J, Cooper R and Reis D J (1994). Agmatine an endogenous clonidine-displacing substance in the brain. Science 263:966-969.

Lin X H, Kashima Y, Khan M, Heller K B, Gu X Z and Sadun A A (1997). An immunohistochemical study of TNF-alpha in optic nerves from AIDS patients. Curr Eye Res 16:1064-1068.

Lingor P, Koeberle P, Kugler S and Bahr M (2005). Down-regulation of apoptosis mediators by RNAi inhibits axotomy-induced retinal ganglion cell death in vivo. Brain 128:550-558.

Lortie M J, Novotny W F, Peterson O W, Vallon V, Malvey K, Mendonca M, Satriano J, Insel P, Thomson S C and Blantz R C (1996). Agmatine, a bioactive metabolite of arginine. Production, degradation, and functional effects in the kidney of the rat. J Clin Invest 97:413-420.

Luo X, Lambrou G N, Sahel J A and Hicks D (2001). Hypoglycemia induces general neuronal death, whereas hypoxia and glutamate transport blockade lead to selective retinal ganglion cell death in vitro. Invest Opthalmol V is Sci 42:2695-2705.

Madigan M C, Sadun A A, Rao N S, Dugel P U, Tenhula W N and Gill P S (1996). Tumor necrosis factor-alpha (TNF-alpha)-induced optic neuropathy in rabbits, Neurol Res 18:176-184. Maher P and Hanneken A (2005). The molecular basis of oxidative stress-induced cell death in an immortalized retinal ganglion cell line. Invest Opthalmol V is Sci 46:749-757.

Maier P C, Funk J, Schwarzer G, Antes G and Falck-Ytter Y T (2005). Treatment of ocular hypertension and open angle glaucoma: meta-analysis of randomised controlled trials. BMJ 331:134-136.

Mansour-Robaey S, Clarke D B, Wang Y C, Bray G M and Aguayo A J (1994). Effects of ocular injury and administration of brainderived neurotrophic factor on survival and regrowth of axotomized retinal ganglion cells. Proc Natl Acad Sci USA 91:1632-1636.

Martin K R, Quigley H A, Zack D J, Levkovitch-Verbin H, Kielczewski J, Valenta D, Baumrind L, Pease M E, Klein R L and Hauswirth W W (2003). Gene therapy with brain-derived neurotrophic factor as a protection: retinal ganglion cells in a rat glaucoma model. Invest Opthalmol V is Sci 44:4357-4365.

Moinard C, Cynober L and de Bandt J P (2005). Polyamines: metabolism and implications in human diseases. Clin Nutr 24:184-197.

Moreau T, Coles A, Wing M, Isaacs J, Hale G, Waldmann H and Compston A (1996). Transient increase in symptoms associated with cytokine release in patients with multiple sclerosis. Brain 119:225-237.

Netland P A, Chaturvedi N and Dreyer E B (1993). Calcium channel blockers in the management of low-tension and open-angle glaucoma. Am J Opthalmol 115:608-613.

Neufeld A H, Das S, Vora S, Gachie E, Kawai S, Manning P T and Connor J R (2002). A prodrug of a selective inhibitor of inducible nitric oxide synthase is neuroprotective in the rat model of glaucoma. J Glaucoma 11:221-225.

Okisaka S, Murakami A, Mizukawa A and Ito J (1997). Apoptosis in retinal ganglion cell decrease in human glaucomatous eyes. Jpn J Opthalmol 41:84-88.

Olmos G, DeGregorio-Rocasolano N, Paz Regalado M, Gasull T, Assumpcio Boronat M, Trullas R, Villarroel A, Lerma J and Garcia-Sevilla J A (1999). Protection by imidazol(ine) drugs and agmatine of glutamate-induced neurotoxicity in cultured cerebellar granule cells through blockade of NMDA receptor. Br J Pharmacol 127:1317-1326.

Osborne N N, Ugarte M, Chao M, Chidlow G, Bae J H, Wood JP and Nash M S (1999). Neuroprotection in relation to retinal ischemia and relevance to glaucoma. Sury Opthalmol 43:S102-128.

Pease M E, McKinnon S J, Quigley H A, Kerrigan-Baumrind L A and Zack D J (2000). Obstructed axonal transport of BDNF and its receptor TRKB in experimental glaucoma. Invest Opthalmol V is Sci 41:764-774.

Qin Q, Patil K and Sharma S C (2004). The role of Bax-inhibiting peptide in retinal ganglion cell apoptosis after optic nerve transection. Neurosci Lett 372:17-21.

Quaranta L, Bettelli S, Uva M G, Semeraro F, Turano R and Gandolfo E (2003). Effect of *ginkgo biloba* extract on preexisting visual field damage in normal tension glaucoma. Opthalmology 110:359-362.

Quigley H A, McKinnon S J, Zack D J, Pease M E, Kerrigan-Baumrind L A, Kerrigan D F and Mitchell R S (2000). Retrograde axonal transport of bdnf in retinal ganglion cells is blocked by acute iop elevation in rats. Invest Opthalmol Vis Sci 41:3460-3466.

Quigley H A, Nickells R W, Kerrigan L A, Pease M E, Thibault D J and Zack D J (1995). Retinal ganglion cell death in experimental glaucoma and after axotomy occurs by apoptosis. Invest Opthalmol V is Sci 36:774-786.

Reis D J and Regunathan S (2000). Is agmatine a novel neurotransmitter in brain? Trends Pharmacol Sci 21:187-193.

Resnikoff S, Pascolini D, Etya'ale D, Kocur I, Pararajasegaram R, Pokharel G P and Mariotti S P (2002). Global data on visual impairment in the year 2002. Bull World Health Organ 82:844-851.

Sawada A, Kitazawa Y, Yamamoto T, Okabe I and Ichien K (1996). Prevention of visual field defect progression with brovincamine in eyes with normal-tension glaucoma. Opthalmology 103:283-288.

Sawada M, Imamura K, Nagatsu T (2006). Role of cytokines in inflammatory process in Parkinson's disease. J Neural Transm Suppl 373-381.

Schori H, Kipnis J, Yoles E, WoldeMussie E, Ruiz G, Wheeler L A and Schwartz M (2001). Vaccination for protection of retinal ganglion cells against death from glutamate cytotoxicity and ocular hypertension: implications for glaucoma. Proc Natl Acad Sci USA 98:3398-3403.

Sener A, Lebrun P, Blachier F and Malaisse W J (1989). Stimulus-secretion coupling of arginine-induced insulin release. Insulinotropic action of agmatine. Biochem Pharmacol 38:327-330.

Su R B, Li J and Qin B Y (2003). A biphasic opioid function modulator agmatine. Acta Pharmacol Sin 24:631-636.

Tabor C W and Tabor H (1984). Polyamines. Annu Rev Biochem 53:749-790.

Tarkowski E, Andreasen N, Tarkowski A and Blennow K (2003). Intrathecal inflammation precedes development of Alzheimer's disease. J Neurol Neurosurg Psychiatry 74:1200-1205.

Tezel G, Li L Y, Patil R V and Wax M B (2001). TNF-alpha and TNF-alpha receptor-1 in the retina of normal and glaucomatous eyes. Invest Opthalmol V is Sci 42:1787-1794.

Tezel G and Wax M B (2000). Increased production of tumor necrosis factor-alpha by glial cells exposed to simulated ischemia or elevated hydrostatic pressure induces apoptosis in cocultured retinal ganglion cells. J Neurosci 20:8693-8700.

Tezel G and Yang X (2004). Caspase-independent component of retinal ganglion cell death, in vitro. Invest Opthalmol Vis Sci 45:4049-4059.

Tezel G, Yang X, Yang J and Wax M B (2004). Role of tumor necrosis factor receptor-1 in the death of retinal ganglion cells following optic nerve crush injury in mice. Brain Res 996:202-212.

Toris C B, Gleason M L, Camras C B and Yablonski M E (1995). Effects of brimonidine on aqueous humor dynamics in human eyes. Arch Opthalmol 113:1514-1517.

Vorwerk C K, Lipton S A, Zurakowski D, Hyman B T, Sabel BA and Dreyer E B (1996). Chronic low-dose glutamate is toxic to retinal ganglion cells: toxicity blocked by memantine. Invest Opthalmol V is Sci 37:1618-1624.

Wang W P, Iyo A H, Miguel-Hidalgo J, Regunathan S and Zhu MY (2006). Agmatine protects against cell damage induced by NMDA and glutamate in cultured hippocampal neurons. Brain Res 1084:210-216.

Weibel D, Kreutzberg G W and Schwab M E (1995). Brain-derived neurotrophic factor (BDNF) prevents lesion-induced axonal die-back in young rat optic nerve. Brain Res 679:249-254.

Werner E B and Drance S M (1977). Progression of glaucomatous field defects despite successful filtration. Can J Opthalmol 12:275-280.

Wheeler L, WoldeMussie E and Lai R (2003). Role of alpha-2 agonists in neuroprotection. Sury Opthalmol 48:S47-S51.

WoldeMussie E, Ruiz G, Wijono M and Wheeler L A (2001). Neuroprotection of retinal ganglion cells by brimonidine in rats with laser-induced chronic ocular hypertension. Invest Opthalmol V is Sci 42:2849-2855.

Yan X, Tezel G, Wax M B and Edward D P (2000). Matrix metalloproteinases and tumor necrosis factor alpha in glaucomatous optic nerve head. Arch Opthalmol 118:666-673.

Yang X C and Reis D J (1999). Agmatine selectively blocks the N-methyl-D-aspartate subclass of glutamate receptor channels in rat hippocampal neurons. J Pharmacol Exp Ther 288:544-549.

Yoshida S, Yoshida A and Ishibashi T (2004). Induction of IL-8, MCP-1, and bFGF by TNF-alpha in retinal glial cells: implications for retinal neovascularization during postischemic inflammation. Graefes Arch Clin Exp Opthalmol Yu C G, Fairbanks C A, Wilcox G L and Yezierski R P (2003). Effects of agmatine, interleukin-10, and cyclosporin on spontaneous pain behavior after excitotoxic spinal cord injury in rats. J Pain 4:129-140.

Yu C G, Marcillo A E, Fairbanks C A, Wilcox G L and Yezierski R P (2000). Agmatine improves locomotor function and reduces tissue damage following spinal cord injury. Neuroreport 11:3203-3207.

Yuan L and Neufeld A H (2000). Tumor necrosis factor-alpha: a potentially neurodestructive cytokine produced by glia in the human glaucomatous optic nerve head. Glia 32:42-50.

Yuan L and Neufeld A H (2001). Activated microglia in the human glaucomatous optic nerve head. J Neurosci Res 64:523-532.

Zhu M Y, Piletz J E, Halaris A and Regunathan S (2003). Effect of agmatine against cell death induced by NMDA and glutamate in neurons and PC12 cells. Cell Mol Neurobiol 23:865-872.

Zhu M Y, Wang W P and Bissette G (2006). Neuroprotective effects of agmatine against cell damage caused by glucocorticoids in cultured rat hippocampal neurons. Neuroscience 141:2019-2027.

The invention claimed is:

1. A method of treating an eye disease in an animal, the method comprising:
   suppressing hypoxic induction activity of c-Jun N-terminal Kinase (JNK) in an animal by administering a therapeutically effective amount of a composition comprising agmatine or a pharmaceutically allowable salt thereof to the animal in need thereof.

2. The method of claim 1, further comprising:
   suppressing Nuclear Factor-kappa B (NF-κB) in an animal.

3. The method of claim 1, wherein the eye disease is associated with apoptosis of retinal ganglion cells in the animal.

4. The method of claim 3, wherein the apoptosis of retinal ganglion cells is induced by hypoxia.

5. The method of claim 3, wherein the apoptosis of retinal ganglion cells is induced by TNF-α.

6. The method of claim 1, wherein the therapeutically effective amount of the composition is 0.1-1.0% by weight of the composition.

7. The method of claim 1, wherein the eye disease is glaucoma, retinopathy, or optic neuropathy.

8. The method of claim 7, wherein the retinopathy is ischemic retinopathy.

9. The method of claim 7, wherein the optic neuropathy is ischemic neuropathy, traumatic optic neuropathy, or AIDS-related optic neuropathy.

10. The method of claim 1, further comprising:
    treating a disease selected from the group consisting of glaucoma, ischemic retinopathy, ischemic optic neuropathy, traumatic optic neuropathy, and AIDS-related optic neuropathy.

* * * * *